(12) United States Patent
Jackson, Jr. et al.

(10) Patent No.: US 10,222,361 B2
(45) Date of Patent: *Mar. 5, 2019

(54) INTEGRATED SYSTEMS AND METHODS OF EVALUATING CANNABIS AND CANNABINOID PRODUCTS FOR PUBLIC SAFETY, QUALITY CONTROL AND QUALITY ASSURANCE PURPOSES

(71) Applicant: VYRIPHARM LLC, Houston, TX (US)

(72) Inventors: Elias Bernard Jackson, Jr., Houston, TX (US); Jerry L. Bryant, Jr., Houston, TX (US)

(73) Assignee: VYRIPHARM LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/470,562

(22) Filed: Mar. 27, 2017

(65) Prior Publication Data

US 2017/0199168 A1   Jul. 13, 2017

Related U.S. Application Data

(63) Continuation of application No. 14/312,051, filed on Jun. 23, 2014, now Pat. No. 9,632,069.
(Continued)

(51) Int. Cl.
*G01N 33/00* (2006.01)
*G01N 33/15* (2006.01)
*G01N 33/94* (2006.01)

(52) U.S. Cl.
CPC ......... *G01N 33/0098* (2013.01); *G01N 33/15* (2013.01); *G01N 33/948* (2013.01)

(58) Field of Classification Search
CPC ...... G06F 19/366; G06F 19/28; G06F 19/326; G06F 17/30289; G06F 17/30864
(Continued)

(56) References Cited

U.S. PATENT DOCUMENTS 5,532,131 A    7/1996 Lewis
6,806,090 B1   10/2004 Holmes et al.
(Continued)

FOREIGN PATENT DOCUMENTS

CN    102749348 A    10/2012
WO    2012071389 A2   5/2012

OTHER PUBLICATIONS

Ali, et al., Evaluation of a Method to Determine the Natural Occurfence of Aflatoxins in Commercial Traditional Herbal Medicines from Malaysia and Indonesia, Elsevier Lid., 2005 (pp. 1763-1772). (10 pages).
(Continued)

*Primary Examiner* — Angelica Ruiz
(74) *Attorney, Agent, or Firm* — Bracewell LLP; Jonathan R. Spivey; Karthika Perumal (57) ABSTRACT

Embodiments of the invention include integrated systems and methods of evaluating *cannabis* and cannabinoid products for public safety, quality control and quality assurance purposes for research and public use purposes. Embodiments of the invention facilitate suppliers and consumers of a *cannabis* and/or cannabinoid product to evaluate the origin, efficacy, potency, and quality of the product. Embodiments of the invention also include *cannabis* processing center where samples of the products are analyzed for research studies to test and set parameters for third parties. Embodiments of the invention include, for example, analyzing *cannabis* products to determine quality and quantity of desired components and undesired components, deter-
(Continued)

mining concentrations of cannabinoids in the product, and comparing measures of components in the product against regulations. Embodiments of the invention further include, for example, an online testing facility for determine whether *cannabis* products meet a plurality of regulations or guidelines.

21 Claims, 3 Drawing Sheets

Related U.S. Application Data (60) Provisional application No. 61/939,385, filed on Feb. 13, 2014, provisional application No. 61/936,200, filed on Feb. 5, 2014.

(58) Field of Classification Search
USPC .......... 707/600–831, 899, 999.001–999.206
See application file for complete search history.

(56) References Cited

U.S. PATENT DOCUMENTS

| | | |
|---|---|---|
| 7,682,798 B2 | 3/2010 | Thompson et al. |
| 7,964,224 B2 | 6/2011 | Beavers |
| 8,486,464 B2 | 7/2013 | Yan et al. |
| 2003/0050334 A1 | 3/2003 | Murty et al. |
| 2003/0113797 A1 | 6/2003 | Jia et al. |
| 2005/0065732 A1 | 3/2005 | Tilton et al. |
| 2006/0192098 A1 | 8/2006 | Danylewych-May |
| 2007/0077660 A1 | 4/2007 | Glas |
| 2008/0286881 A1 | 11/2008 | Apel et al. |
| 2010/0119606 A1 | 5/2010 | Whittle et al. |
| 2010/0286993 A1 | 11/2010 | Lovelace |
| 2011/0040486 A1 | 2/2011 | Dadala et al. |
| 2012/0271739 A1 | 10/2012 | Billingsley et al. |
| 2012/0311744 A1 | 12/2012 | Sirkowski |
| 2013/0337477 A1 | 12/2013 | Kuhr et al. |
| 2014/0287068 A1 | 9/2014 | Lewis et al. |

OTHER PUBLICATIONS

CannLabs, Cannabis Testing, Marijuana Testing, Cannabis Science & Potency, 2014. (5 pages).
CannLabs, Extraction, Marijuana Potency Testing, CBD & THC Test Lab, 2014. (5 pages).
CannLabs, Guide to CBD, Marijuana Testing, Cannabis Science & Potency, 2014. (4 pages).
CannLabs, Heavy Metals, 2014. (3 pages).
CannLabs, Latest Test Results, 2014. (13 pages).
CannLabs, Marijuana Potency Testing, CBD & THC Test Lab, Cannabinoids, 2014. (3 pages).
Halford, Bethany, Analyzing Cannabis, C&EN Boston, Dec. 9, 2013, pp. 32-33. (2 pages).
International Search Report & Written Opinion for PCT/US2015/014594 dated Jun. 19, 2015.
Sexton, Michelle et al., Sampling Cannabis for Analytical Purposes, BOTEC Analysis Corp., Nov. 15, 2013. (26 pages).

INTEGRATED SYSTEMS AND METHODS OF EVALUATING CANNABIS AND CANNABINOID PRODUCTS FOR PUBLIC SAFETY, QUALITY CONTROL AND QUALITY ASSURANCE PURPOSES

RELATED APPLICATIONS

This application claims the benefit of and priority to U.S. Provisional Patent Application No. 61/936,200, filed on Feb. 5, 2014, and titled "Systems and Methods of Evaluating *Cannabis* Products for Public Safety, Quality Control and Quality Assurance Purposes"; and U.S. Provisional Patent Application No. 61/939,385, filed on Feb. 13, 2014, and titled "Systems and Methods of Evaluating *Cannabis* Products for Public Safety, Quality Control and Quality Assurance Purposes", the disclosures of which are each hereby incorporated by reference in their entireties.

BACKGROUND

1. Field of the Invention

Embodiments of the present invention relate generally to the field of testing natural products such as *cannabis* and cannabinoid products for quality control and quality assurance purposes. More specifically, embodiments of the present invention facilitate a supplier or a consumer of a *cannabis* and/or cannabinoid product to evaluate the origin, efficacy, potency, and quality of the product. Embodiments of the invention also relate to a *cannabis* and cannabinoid processing center where samples of the products are analyzed for public safety, quality control and quality assurance purposes.

2. Description of Related Art

*Cannabis* and cannabinoid products are legally available for human consumption for several purposes, including, but not limited to, medicinal, research and recreational purposes. Undesired and in some cases toxic chemicals, including pesticides and plant growth regulators, tag along with the *cannabis* products and threaten the health of the consumers. As some *cannabis* products can be inhaled rather than eaten, any toxins carried by the products have a direct route into the lungs and blood stream of the consumer. Some states have regulations for controlling the environment where the *cannabis* plants are grown. Most states where *cannabis* products can be legally obtained, have no means for ensuring that the plants are grown under controlled environments. In addition to natural contamination during growth of the plants, *cannabis* and cannabinoid products are unscrupulously contaminated by using extracts or dried parts of other plants, glass particles, industrial chemicals, sugar or sand, and other micro contaminants. There are no robust integrated systems to ensure that the *cannabis* and cannabinoid products are free of chemical and microbiological contamination, and that the product can be traced as the plant is grown, processed into products, and moved to stores for public consumption. Most consumers do not have access to *cannabis* or cannabinoid products that have been tested for purity by third party validated labs.

SUMMARY

The Applicants recognize the public health and safety risks that exist when *cannabis* or cannabinoid products are not subjected to adequate research activities that should be performed in labs that have good laboratory practices, current good manufacturing practices, quality testing and quality assurance procedures and do not have adequate labeling regarding the contents. Undesired and in some cases toxic chemicals, including pesticides and plant growth regulators, tag along with *cannabis* and cannabinoid products and threaten the health and safety of the consumers, so additional research activities may be needed to test the unknown of the many species of the products. Embodiments of the invention include, for example, a *cannabis* processing center where samples of *cannabis* and cannabinoid products are analyzed for research studies to test and set parameters for third parties, such as government agencies for grant awards, public safety, quality control and quality assurance purposes.

Exemplary embodiments of the present invention include a method for evaluating one or more *cannabis* and cannabinoid products for use in a particular industry for research, pubic use, or a combination thereof. In certain embodiments, the method contains the steps of receiving a *cannabis* or cannabinoid product from a supplier and subjecting the product to a battery of testing protocols for research activities that should be performed in labs that have good laboratory practices, current good manufacturing practices to set standards and parameters for research studies, in vitro, in vivo both for non-human and human (public) consumptions. These testing protocols measure the quality and quantity of desired components and undesired components in the product, and compare these measurements of the quality and quantity of desired components and undesired components in the *cannabis* or cannabinoid product against appropriate standards in a particular industry. In certain embodiments, the method may also include steps of certifying that the *cannabis* or cannabinoid product meets or fails to meet the standards. Research activity may be warrant through a grant from a government agency, so that additional information may be gathered for public safety.

By way of example, an embodiment of the invention can include a method for evaluating a *cannabis* or cannabinoid product for use in a particular industry for research or public use. An embodiment of this method includes the steps of analyzing a *cannabis* or cannabinoid product, measuring quality and quantity of desired components and undesired components in the product, and comparing measurements of the quality and quantity of desired components and undesired components in the product against appropriate standards in a particular industry for research or public use. For example, embodiments of the invention can test the amount of cannabinoids in a product and compare it against state or federal regulations or standards. By a way of example, an embodiment of the invention can include measuring the quality or quantity of THC in edible products and certifying or producing a label that indicates that that the tested product meets appropriate regulations such as having no more than 100 milligram of THC in an edible *cannabis* product.

In another embodiment, this method can also include the steps of certifying that the *cannabis* or cannabinoid product satisfies or fails to satisfy the appropriate standards. In another embodiment, this method can also include the step of measuring quality and quantity of desired components and undesired components in the *cannabis* or cannabinoid product by performing one or more of microbiological testing, analytical testing, food testing, acidified food testing, liquid testing, pathogen testing, quality control testing, quality assurance testing, or combinations thereof for research or for public use.

By way of example, an embodiment of the invention can include an online *cannabis* and cannabinoid testing system (collectively referred to as a *cannabis* testing system). An embodiment of this system includes one or more processors, an input/output unit adapted to be in communication with the one or more processors, one or more *cannabis* databases in communication with the one or more processors to store and associate a plurality of regulatory guidelines with a plurality of measurements of quality and quantity of desired components and undesired components in a *cannabis* product, one or more electronic interfaces positioned to display an online user report and defining one or more *cannabis* user interfaces; and non-transitory computer-readable medium positioned in communication with the one or more processors and having one or more computer programs stored thereon. The computer program includes a set of instructions that when executed by one or more processors cause the one or more processors to perform operations of generating the *cannabis* user interface to display to a user thereof one or more online *cannabis* user reports, the *cannabis* user interface allowing an input of a plurality of information associated with the user or with the *cannabis* product, determining whether the *cannabis* product meets the regulatory guidelines responsive to receiving the plurality of information associated with the user or with the *cannabis* product and information from the one or more *cannabis* databases, associating the plurality of regulatory guidelines with the plurality of measurements of quality and quantity of desired components and undesired components in a *cannabis* product, and outputting to the one or more *cannabis* user interfaces the one or more online *cannabis* user reports, the *cannabis* user reports including one or more of the plurality of information associated with the user or with the *cannabis* product, and one or more of the plurality of measurements of quality and quantity of desired components and undesired components in a *cannabis* product for research or for public use.

BRIEF DESCRIPTION OF THE DRAWINGS

So that the manner in which the features and benefits of the invention, as well as others which will become apparent, may be understood in more detail, a more particular description of the embodiments of the invention may be had by reference to the embodiments thereof which are illustrated in the appended drawings, which form a part of this specification. It is also to be noted, however, that the drawings illustrate only various embodiments of the invention and are therefore not to be considered limiting of the invention's scope as it may include other effective embodiments as well.

DETAILED DESCRIPTION

The present invention will now be described more fully hereinafter with reference to the accompanying drawings, which illustrate various embodiments of the invention. This invention, however, may be embodied in many different forms and should not be construed as limited to the embodiments set forth herein. Rather, these embodiments are provided so that this disclosure will be thorough and complete, and will fully convey the scope of the invention to those skilled in the art. It is to be fully recognized that the different teachings of the various embodiments discussed below may be employed separately or in any suitable combination to produce desired results. The various characteristics mentioned above, as well as other features and characteristics described in more detail below, will be readily apparent to those skilled in the art upon reading the following detailed description of the various embodiments, and by referring to the accompanying drawings. In the drawings and description that follow, like parts are marked throughout the specification and drawings with the same reference numerals, respectively. The prime notation, if used, indicates similar elements in alternative embodiments. The drawings are not necessarily to scale. Certain features of the disclosure may be shown exaggerated in scale or in somewhat schematic form and some details of conventional elements may not be shown in the interest of clarity and conciseness.

Exemplary embodiments of the present invention advantageously provide, for example, systems, computer-readable program products, and related methods to test *cannabis* and cannabinoid products.

As used herein, a *cannabis* product includes, but is not limited to, any useable product legally intended for research or for human consumption, and containing one or more of Δ-9-tetrahydrocannabinol, 8-tetrahydrocannabinol, cannabichromene, cannabicyclol, cannabidiol, cannabielsoin, cannabigerol, cannabinidiol, cannabinol, cannabitriol, and cannabidiolic acid. *Cannabis* products can include two or more of these cannabinoids in varying proportions. *Cannabis* products can include products that are infused with one or more of the above-identified cannabinoids and are legally intended for human consumption. *Cannabis* products can include products obtained from naturally occurring or genetically modified plants that are scientifically identified as *Cannabis sativa, Cannabis indica*, and *Cannabis ruderalis*. *Cannabis* products can include products synthesized in a laboratory and containing one or more of Δ-9-tetrahydrocannabinol, 8-tetrahydrocannabinol, cannabichromene, cannabicyclol, cannabidiol, cannabielsoin, cannabigerol, cannabinidiol, cannabinol, cannabitriol, cannabidiolic acid, nabilone, and endocannabinoids like 2-archidonoylglycerol, n-archidonoyldopamine, virodhamine, and noladin ether. A *cannabis* product can include products that are processed to include one or more of the sixty different cannabinoids that have been identified in samples of *cannabis* obtained from naturally occurring or genetically modified plants that are scientifically identified as *Cannabis sativa, Cannabis indica*, and *Cannabis ruderalis*. Embodiments of the invention also include the testing of cannabinoid products that are isolated from *cannabis* as understood by those skilled in the art. Accordingly, a *cannabis* product as used herein further includes products that include one or more cannabinoids isolated from *cannabis*.

*Cannabis* products can come in a variety of forms, including: as a dried plant, resin, in powder form, as oil, as products for smoking, as vaporized products, and also as *cannabis*-infused teas, candies, cookies, and brownies. *Cannabis* products can contain *cannabis* compounds derived from natural sources or otherwise and incorporated along with organic or inorganic components, including, but not limited to, natural, polar, or non-polar solvents. *Cannabis* products can be used for medicinal purposes, research purposes, recreational purposes, or for a combination thereof.

A *cannabis* product that is evaluated under embodiments of the invention can be received from a variety of sources, including, but not limited to, producers and processors of the *cannabis* products and wholesale and retail sales entities of the *cannabis* products. As used herein, producers include a person or an entity authorized by a state or federal control board or agency to grow, plant, cultivate, harvest, or be similarly involved in production of naturally occurring or genetically modified plants that are scientifically identified as *Cannabis sativa, Cannabis indica*, and *Cannabis ruderalis*. Producers also include a person or an entity authorized by a state or federal control board or agency to procure raw materials, and chemically manufacture, or be similarly involved in production of *cannabis* products.

As used herein, a processor of a *cannabis* product can include, but is not limited to, a person or an entity authorized by a state or federal control board or agency to process naturally occurring or chemical raw materials to produce *cannabis* products, package and label *cannabis* products for sale in retail outlets, and sell *cannabis* products to wholesale and retail sales entities.

As used herein, a retail sales entity of a *cannabis* product can include, but is not limited to, a person or an entity authorized by a state or federal control board or agency to sell *cannabis* products in a retail outlet. As used herein, a retail outlet can include, but is not limited to, a location authorized by a state or federal control board or agency for the retail sale of *cannabis* products. For example, without limitations, federal agencies such as the US Department of Agriculture, the Food and Drug Administration, and the Drug Enforcement Agency can regulate the consumption of the *cannabis* products and provide the required guidelines for testing the *cannabis* products. For example, without limitations, retail sales entities in the state of Washington include entities that sell *cannabis* products under a license from the Washington Liquor Control Board. For example, without limitations, retail sales entities in the state of Colorado include entities that sell *cannabis* products under a license from the Marijuana Enforcement Division.

As used herein, users can include, but is not limited to, persons or entities who use or benefit from certain embodiments of the invention by receiving information regarding the *cannabis* products. Users can also include producers of the plant, manufacturers and distributors of the *cannabis* products, researchers at government and private entities, and wholesale and retail sales entities of the *cannabis* products. Users can also include persons or entities who receive through legal means the *cannabis* products from producers of the plant, manufacturers and distributors of the *cannabis* products, and wholesale and retail sales entities of the *cannabis* products. Users can also include, but are not limited to, people who consume the *cannabis* product for medicinal or recreational purposes, or for any legally approved reason. Users can also include, but are not limited to, individuals who are employees or agents of governmental agencies (such as researchers whom may be performing studies for non-human or human use), and have a legal reason to access the information associated with the *cannabis* products. Information regarding the *cannabis* products involve any or some or all information associated with origin, efficacy, potency, quality and quantity of desired components and undesired components in the *cannabis* products, the governmental licenses and authorizations for the *cannabis* products, or any combinations of the information thereof. Desired components in *cannabis* products include, without limitations, chemical components and biological components of a *cannabis* product that allow the *cannabis* product to meet the requirements for sale in a particular industry. Desired components, for example without limitations, include cannabinoids, pharmaceutical fillers, taste additives, and food coloring. Undesired components in *cannabis* products can include, without limitations, chemical components and biological components of a *cannabis* product that cause the *cannabis* product unfit for sale in a particular industry. Undesired components, for example without limitations, include pathogenic microorganisms and toxic chemicals like pesticides, fertilizers, and plant growth regulators. Desired components in a *cannabis* product in a particular industry may be undesired components in another industry.

In certain embodiments of the invention, a *cannabis* product received from any one or more of the sources described above can be subjected to a variety of testing protocols for research or public use that detect the quality and quantity of desired components and undesired components. A supplier, researcher, or a consumer of one or more *cannabis* products can evaluate the origin, efficacy, potency, and quality of the one or more *cannabis* products through a variety of testing protocols. Quantity of desired components and undesired components in a *cannabis* product can be expressed in terms of absolute weight, absolute volume, or relative weight or relative volume as compared to other components in the *cannabis* product. Testing protocols can include one or more analytical tests and methods of separation, identification, and quantification of the chemical components. For example without limitations, a *cannabis* product can be subjected to a battery of routine analytical tests or to a specialized research study. Testing protocols can include without any limitation, one or more of the following: microbiological testing, analytical testing, food testing, acidified food testing, liquid testing, pathogen testing, quality control, quality assurance, additional testing services, or combinations thereof. Analytical tests, for example without limitations, can include extractables/leachables studies, reference standard characterization, structural elucidation of target/lead compounds, structural elucidation of unknowns, impurity and degradation studies, identification and characterization of the quantity of chemical components, synthesis and purification of impurities and degradation products, and elemental analysis of the *cannabis* products. Analytical tests, for example without limitations, can include tests establishing the cannabinoid profile, and the efficacy and potency of the cannabinoids present, tests determining the dosage delivered by a particular formulation or food product, and tests for producing products with the appropriate dose. The cannabinoid profile includes the identification and quantification of at least the major cannabinoids found within a *cannabis* product. For example, in certain embodiments, determining the quantity of desired components in a *cannabis* product includes determining the concentration of one or more cannabinoids in the one or more *cannabis* products. For example, in certain embodiments, the quantity of desired components like tetrahydrocannabinol (THC) along with other cannabinoids and terpenoids can be determined by either liquid chromatography, mass spectrometry or both. This is especially important for edible forms of *cannabis* products, where a greater percentage of active ingredients reach the bloodstream. Appropriate dosage can bring about medicinal or health benefits to the consumer, while excess or improper dosage can have detrimental side effects.

As used herein, microbiological testing can include but is not limited to testing protocols that detect, for example, the presence of microorganisms, the type of microorganisms, the quantity, or combinations thereof. Examples of microbiological testing include total plate count, aerobic plate count, anaerobic plate count, psychrotrophic plate count, or probiotic testing. Examples of undesired microorganisms include, without limitations, *E. coli*, coliforms, lactic acid bacteria, mesophilic spore formers, mold, yeast, and thermophilic spore formers.

As used herein, food testing can include but is not limited to testing protocols for the food industry that detect the quality and quantity of desired components and undesired components, for example without limitations, the presence of microorganisms, the type of microorganisms, the quantity, or combinations thereof. Examples of food testing include total plate count, aerobic plate count, anaerobic plate count, psychrotrophic plate count, or probiotic testing. Examples of undesired microorganisms include, without limitations, Coliforms, *E. coli, Salmonella, Staphylococcus aureus*, and fungi like yeasts and molds.

As used herein, liquid testing can include but is not limited to testing protocols that test liquids containing *cannabis* products to detect the quality and quantity of desired components and undesired components. For example without limitations, a *cannabis* product in a liquid form can be tested for the presence of microorganisms, the type of microorganisms, the quantity, or combinations thereof. Examples of liquid testing include total plate count, aerobic plate count, anaerobic plate count, or probiotic testing. Examples of undesired microorganisms include, without limitations, coliforms including fecal coliforms, *E. coli, Salmonella, Staphylococcus aureus*, and fungi like yeasts and molds. Certain embodiments of the invention include testing protocols for detecting the presence and quantity of pathogenic microorganisms, for example, without limitations, *Bacillus cereus, Campylobacter, Chronobacter, Clostridium perfringens*, Hemorrhagic *E. coli* (O157: H7), *Listeria monocytogenes*, Non-O157 STEC *E. coli, Salmonella, Staphylococcus aureus, Shigella, Vibrio*, and *Yersinia*.

In certain embodiments of the invention, a *cannabis* product received from any one or more of the sources described above can be subjected to a variety of testing protocols that determine compliance regulatory guidelines from federal and state agencies and boards, including, but not limited to, guidelines for labeling, packaging, compounding, or marketing, or combinations thereof. For example, without limitations, federal agencies that regulate labeling of food products include the FDA and the USDA. Examples of regulatory guidelines also include, without limitations, guidelines regarding labeling, nutritional claims, monitoring and rating of *cannabis* products, or combinations thereof. Another embodiment of the invention, in consultation with one or more federal and state agencies or boards, is a method of establishing appropriate standards for *cannabis* products according to grade, condition, cannabinoid profile, THC concentration, or other qualitative and quantitative measurements deemed acceptable or compliant by the one or more federal and state agencies or boards.

In certain embodiments of the invention, a *cannabis* product received from any one or more of the sources described above can be subjected to a variety of testing protocols to determine compliance with *cannabis* product labeling guidelines from federal and state agencies and boards. For example, without limitations, federal agencies that regulate labeling of food products include the FDA and the USDA. Examples of labeling guidelines include, without limitations, guidelines for the nutrition facts panel, the ingredient statement and allergen declaration, the nutritional claims, the statement of identity, the net contents statement, the type size and placement requirements for the label, and combinations thereof. For example, packaging *cannabis* products for consumption as food must conform to rigorous requirements by federal and state agencies and boards. By utilizing certain embodiments of the invention, one can save time and avoid costly mistakes as a result of improperly labeled food products. By utilizing certain embodiments of the invention, a professional can review and provide direction, and guidance for compliance with regulatory guidelines.

In certain embodiments of the invention, a *cannabis* product received from any one or more of the sources described above can be subjected to a variety of testing protocols to determine the appropriate nutrition facts and prepare labels or reports for compliance with *cannabis* product guidelines from federal and state agencies and boards. For example, without limitations, different *cannabis* products can be consumed in different ways like smoking, vaporizing, eating a food product, drinking a liquid product, or utilizing injectable, sublingual or topical formulations. Labeling *cannabis* products for each of these consumption modalities will require detailed testing regarding the quality and quantity of desired components and undesired components. Certain embodiments of the invention include methods and systems to display on *cannabis* products received from any one or more sources described above, a plurality of identification information associated with the *cannabis* products. For example, by utilizing certain embodiments of the invention, one can develop the appropriate label or report required for the labeling or packaging necessary to prepare *cannabis* products for consumption. Certain embodiments of the invention result in the production of an appropriate nutrition facts panel for a *cannabis* product, including without limitation, the appropriate format and the contents for the panel as required by the regulatory agency or board, like the chemical analysis, the calorific analysis, the ingredient analysis, and combinations thereof. Other identification information associated with the *cannabis* products include source of the *cannabis* products, the particular strains of the *cannabis* plant, and the quality and quantity of desired components in the *cannabis* product. Information on the label can also include the various diseases that can be treated or mitigated using the *cannabis* products, such as but not limited to depression, pain, nausea, headaches, insomnia, galucoma, epileptic seizures, inflammatory bowel diseases, lupus, arthritis, Parkinson's disease, post-traumatic stress disorders, and muscle spasms. These diseases can be acute or chronic in nature. Information on the label can also include one or more beneficial effects associated with the use of *cannabis* products, such as relief from anxiety or pain, improvements in lung health, lessen side effects of other drug treatments, and increase the effectiveness of drug treatments. In certain embodiments of the invention, a user can access a database of *cannabis* products and receive information regarding the *cannabis* products, the nutritional analysis, the source of the ingredients, and details regarding the producers, processors, and sales entities associated with the *cannabis* product.

Certain embodiments of the invention also include labeling of the *cannabis* products with one or more visual indicators associated with the quality and quantity of desired components in the *cannabis* products. Certain embodiments of the invention also include labeling of the *cannabis* products with one or more visual indicators associated with each of the specified ranges of quantity of desired components in the *cannabis* product. Concentration includes, for example, the amount of a particular chemical component as compared to all others from oils, and plants products. The concentrations may be expressed, for example, in one or more of the following ways: percentage of weight/weight; percentage of volume/weight; percentage of volume/volume; percentage of weight/volume; percentage of particular chemical component/total active pharmaceutical ingredients (API(s)); and percentage of API(s)/total chemical component(s). Embodiments of the invention can also be based on *cannabis* plant derived-components or based on cannabinoids in a product. For example, as shown in Table 1, an edible product made from the *cannabis* strain popularly called Pineapple Express contains moderate levels of tetrahydrocannabinol (THC) but low levels of cannabidiol (CBD) and cannabinol (CBN). For example, as shown in Table 2, a *cannabis* product intended for consumption as a vaporizer or smoke, like a *cannabis* concentrate made from the *cannabis* strain popularly called Purple Babba Kush contains high levels of tetrahydrocannabinol (THC) but low levels of cannabidiol (CBD) and cannabinol (CBN). Tables 1 and 2 are exemplary examples and in no way limit embodiments of the invention. Other components that can be analyzed and indicated on the labels of the *cannabis* products include but are not limited to Tetrahydrocannabivarin (THCV), Cannabichromene (CBC), and Cannabicyclol (CBL). Visual indicators can be bars, charts, graphs, symbols, codes or other graphical representations to indicate the relative concentration of one or more components in a *cannabis* product. Visual indicators can also indicate the efficacy or potency of the particular *cannabis* product to treat or mitigate particular illnesses or diseases. Embodiments of the invention can further include, for example, a reference standard calculated for each *cannabis* strain as understood by those skilled in the art and from there a percent (%) value from 0 to 50 percent can be assigned to each of the *cannabis*' API components. (With 0 being the lowest to 50 being the highest concentration % values, along with a moderate/medium concentration in the middle.) Embodiments of the invention allow consumers to make educated decisions regarding which products to consume or purchase based on the desired symptomatic relief or desired beneficial health effect.

TABLE 1

Edible *Cannabis* Products from *cannabis* strain - Pineapple Express.

| Component | Low Concentration | Moderate Concentration | High Concentration |
|---|---|---|---|
| % THC | | | 18% |
| % CBD | 0.19% | | |
| % CBN | <0.05% | | |

TABLE 2

*Cannabis* concentrates consumed through use of vaporizers.

| Component | Low Concentration | Moderate Concentration | High Concentration |
|---|---|---|---|
| % THC | | | 26% |
| % CBD | 0.19% | | |
| % CBN | <0.05% | | |

Certain embodiments of the invention result in the production of an appropriate ingredient statement and allergen declaration for a *cannabis* product, including without limitation, the appropriate format and the contents for the statement and declaration as required by the regulatory agency or board, like the concise order of predominance of ingredients and clear identification of possible allergens.

Certain embodiments of the invention result in the production of appropriate nutritional or marketing claims for a *cannabis* product, including without limitation, the appropriate format and the contents for the nutritional and marketing claims as required by the regulatory agency or board. In certain embodiments of the invention, the user is advised about the nutritional and marketing claim acceptability and appropriate phrasing of the nutritional and marketing claims.

By way of example, an embodiment of the invention can include an online *cannabis* testing system. An embodiment of this system includes one or more processors, an input/output unit adapted to be in communication with the one or more processors, one or more *cannabis* databases in communication with the one or more processors to store and associate a plurality of regulatory guidelines with a plurality of measurements of quality and quantity of desired components and undesired components in a *cannabis* product, one or more electronic interfaces positioned to display an online user report and defining one or more *cannabis* user interfaces; and non-transitory computer-readable medium positioned in communication with the one or more processors and having one or more computer programs stored thereon. The computer program includes a set of instructions that when executed by one or more processors cause the one or more processors to perform operations of generating the *cannabis* user interface to display to an user thereof one or more online *cannabis* user reports, the *cannabis* user interface allowing an input of a plurality of information associated with the user or with the *cannabis* product, determining whether the *cannabis* product meets the regulatory guidelines responsive to receiving the plurality of information associated with the user or with the *cannabis* product and information from the one or more *cannabis* databases, associating the plurality of regulatory guidelines with the plurality of measurements of quality and quantity of desired components and undesired components in a *cannabis* product, and outputting to the one or more *cannabis* user interfaces the one or more online *cannabis* user reports, the *cannabis* user reports including one or more of the plurality of information associated with the user or with the *cannabis* product, and one or more of the plurality of measurements of quality and quantity of desired components and undesired components in a *cannabis* product.

Certain embodiments of the invention integrate the testing results from *cannabis* processing centers with other information associated with the *cannabis* products and thereby address a public need for standardized information and regulation of legal *cannabis* products. Certain embodiments of the invention allow for tracking the identity, quality and quantity of raw materials, and the desired and undesired components in them, as the raw materials—the *cannabis* plants—are processed to finished *cannabis* products, packaged and labeled for wholesale and retail outlets. Certain embodiments of the invention allow for research or public use, federal agencies or state regulatory agencies to regulate consumption and provide further guidelines for testing and regulation as well as allow for consumers to be fully informed of the product they purchase or consume. Package labeling for regulation and accurate information requires the integration of several analytical testing to provide the data and information needed to appropriately certify a product. Certain embodiments of the invention provide governing agencies a way of monitoring and regulating legal distribution of *cannabis* products. By a way of example, an embodiment of the invention can include measuring the quality or quantity of THC (or other cannabinoids) in edible products and certifying or producing a label that indicates that that the tested product meets appropriate regulations such as having no more than 100 milligram of THC in an edible *cannabis* product.

In certain aspects, all testing protocols that detect the quality and quantity of desired components and undesired components in the *cannabis* products can be carried out in one or more *cannabis* processing centers for research purposes, public use purposes, or a combination thereof. These centers are equipped to receive samples of *cannabis* products from a plurality of users, subject the samples of *cannabis* products to the appropriate testing protocols, and deliver a plurality of information associated with the user or with the *cannabis* product. Testing protocols that can be housed in a *cannabis* processing center include without any limitation, one or more of the following: microbiological testing, food testing, acidified food testing, liquid testing, pathogen testing, additional testing services, or combinations thereof. Testing protocols for a *cannabis* product can be performed by one or more *cannabis* processing centers. For example without limitation, one *cannabis* processing center can perform a subset of the testing protocols like microbiological testing and pathogen testing, while another processing center can perform food and nutritional testing on the same samples. A *cannabis* processing center can be remote from or house the one or more *cannabis* databases that store a plurality of regulatory guidelines with a plurality of measurements of quality and quantity of desired components and undesired components in the *cannabis* products. A *cannabis* processing center can also be remote from or house the equipment and personnel required to perform the testing protocols to determine whether the *cannabis* products meet the regulatory guidelines. A *cannabis* processing center can also be remote from or house the equipment and personnel required to perform the testing protocols to determine the quality and quantity of desired components and undesired components in the *cannabis* products. The *cannabis* processing centers can be certified testing centers that comply with the guidelines and regulations from state or federal control boards or agencies including but not limited to the US Department of Agriculture, the Food and Drug Administration, and the Drug Enforcement Agency.

According to an exemplary embodiment of the invention, the *cannabis* processing center includes one or more labs that have good laboratory practices and current good manufacturing practices set by federal or state agencies as understood by those skilled in the art to performing quality testing and quality assurance procedures. Embodiments of the invention including analyzing *cannabis* and cannabinoid products for research studies to test and set parameters for third parties, such as government agencies, for grant awards, public safety, quality control and quality assurance purposes.

Figure 1:
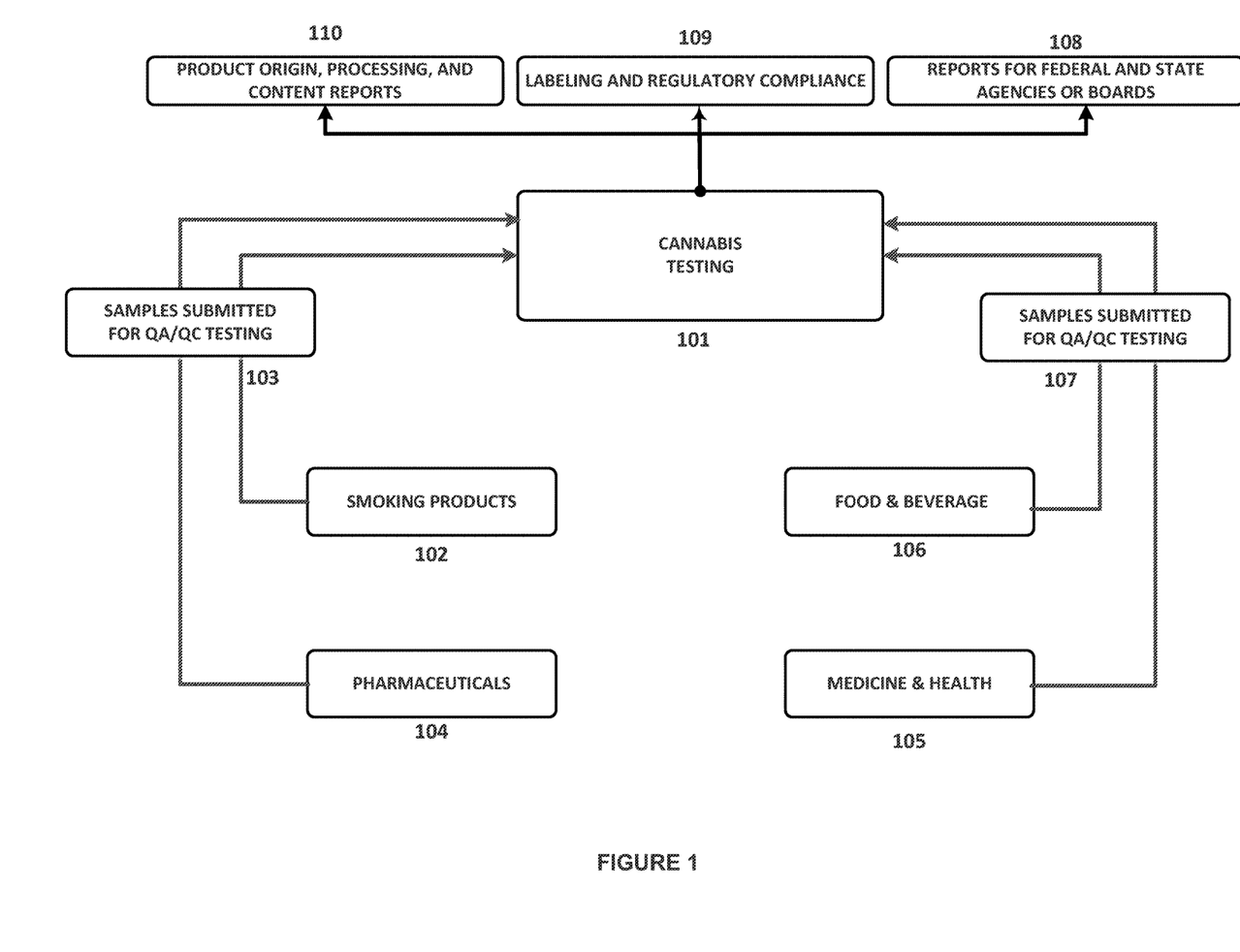
FIG. 1 is a schematic block diagram of an exemplary method according to an embodiment of the invention.

FIG. 1 is an illustration of an exemplary embodiment of the methods of the invention. In one embodiment, the method involves the use of *cannabis* testing procedures 101. In a further embodiment, the *cannabis* testing procedures can be housed in a *cannabis* processing center. Users of this embodiment of the invention submit samples of their *cannabis* products for testing. These *cannabis* testing procedures 101 detect the quality and quantity of desired components and undesired components in the *cannabis* products. Testing protocols include without any limitation, one or more of the following: microbiological testing, food testing, acidified food testing, liquid testing, pathogen testing, additional testing services, or combinations thereof. For example, users of *cannabis* smoking products 102 can submit their samples for quality control and quality assurance testing 103. In certain embodiments of the invention, users of *cannabis* pharmaceutical products 104 can submit their samples for quality control and quality assurance testing 103. In certain embodiments of the invention, users of *cannabis* food and beverage products 106 can submit their samples for quality control and quality assurance testing 107. In certain embodiments of the invention, users of *cannabis* medicinal or health products 105 can submit their samples for quality control and quality assurance testing 107.

In certain embodiments of the invention, users can access a variety of information, recommendations, and advisory reports 109 relating to labeling and regulatory compliance aspects of *cannabis* products submitted for testing. Users of certain embodiments of the invention can access a variety of information and reports 110, including, but not limited to, reports regarding the origin and processing records, the chemical and biological contents of the *cannabis* products submitted for testing. Certain embodiments of the invention include users like federal and state agencies or boards accessing the information to generate reports 108, including, but not limited to, reports regarding the various *cannabis* products available in the various industries, production and processing volumes of the various products, the producers of the various products, and their compliance to the laws and regulatory guidelines. Information from certain embodiments of the invention, like the database with all the product data, is important in helping producers, processors, and sellers sustain or improve their product and their performance in the supply chain, and for making decisions regarding which producers, processors, and sellers can be relied on to meet specified requirements of the consumers, or the appropriate regulatory agencies or boards. In certain embodiments of the invention, a *cannabis* product received from any one or more of the sources described above can be subjected to a variety of testing protocols to help federal and state agencies and boards with conducting safety assessments and recalls of the *cannabis* products, and other enforcement actions.

Figure 2:
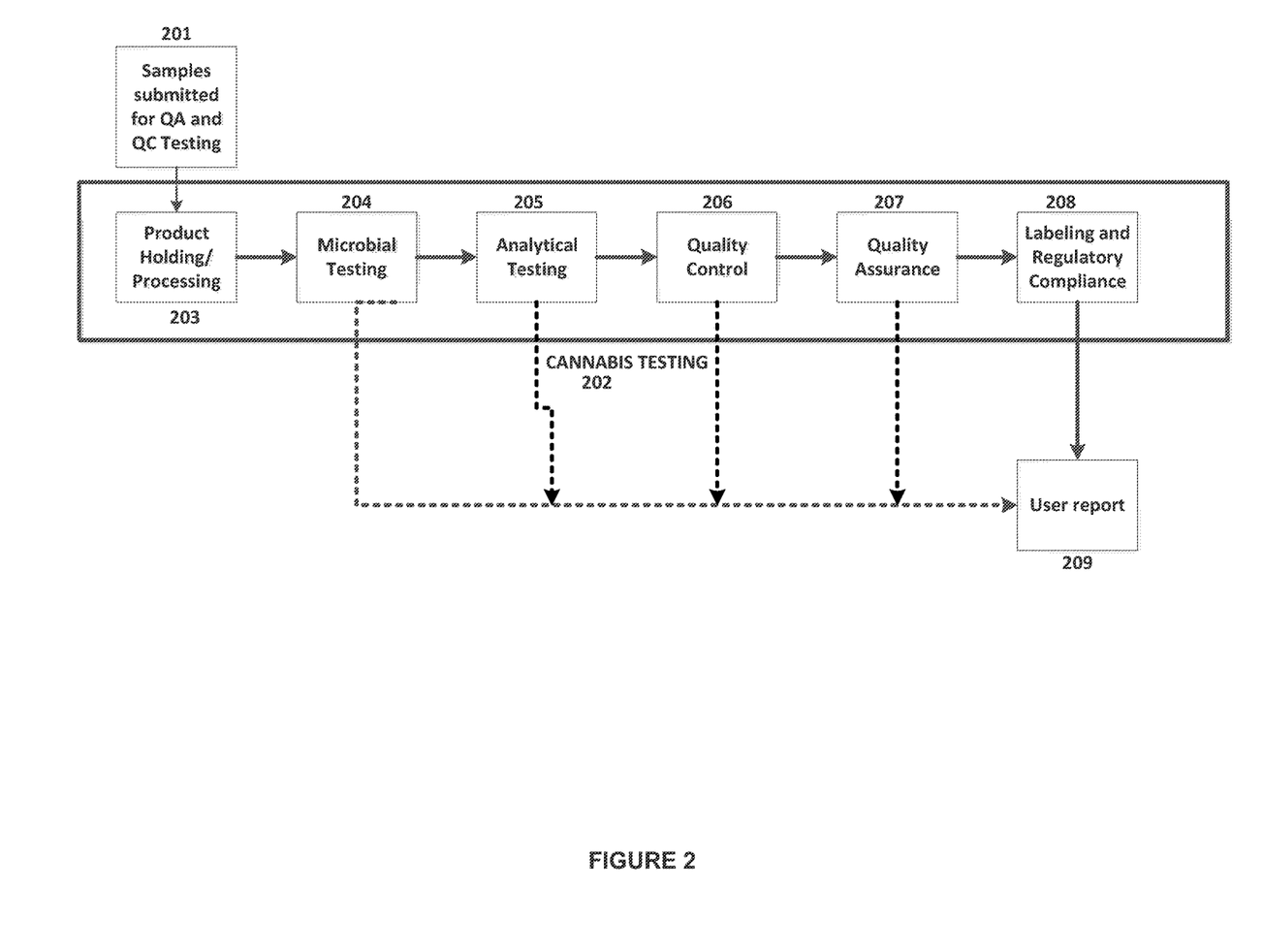
FIG. 2 is a schematic block diagram of an exemplary method according to an embodiment of the invention.

FIG. 2 is an illustration of an exemplary embodiment of the methods of the invention. Samples are submitted by users 201 for quality control testing, quality assurance testing, or both quality assurance and quality control testing. In certain embodiments of the invention, these samples can be initially processed 203 for the appropriate testing procedures 202. In other embodiments of the invention, the samples can be directly utilized in any of the testing procedures 202 that detect the quality and quantity of desired components and undesired components. Testing protocols include without any limitation, one or more of the following: microbial testing, analytical testing, food testing, acidified food testing, liquid testing, pathogen testing, additional testing services, or combinations thereof. In certain embodiments of the invention, these samples are subjected to microbial testing 204 that detect, for example without limitations, the presence of microorganisms, the type of microorganisms, the quantity, or combinations thereof.

In certain embodiments of the invention, these samples are subjected to analytical testing procedures 205 that detect the quality and quantity of desired components and undesired components. Analytical tests, for example without limitations, can include extractables/leachables studies, reference standard characterization, structural elucidation of target/lead compounds, structural elucidation of unknowns, impurity and degradation studies, identification and characterization of the quantity of chemical components, synthesis and purification of impurities and degradation products, and elemental analysis of the *cannabis* products.

In certain embodiments of the invention, these samples are subjected to quality control tests 206. Quality control testing ensures that *cannabis* products of a high quality, good safety profile and with the desired potency are supplied to the public, for their good health and for the economic benefits derived from trade of safe *cannabis* products. In certain embodiments of the invention, the samples subjected to quality control tests range from the raw materials to finished products. In certain embodiments of the invention, testing can be conducted to ensure that products at each step of the *cannabis* product supply chain meet quality and safety standards specified by the appropriate regulatory agencies or boards.

In certain embodiments of the invention, these samples are subjected to quality assurance tests 207. Quality assurance is a comprehensive program designed to ensure that one or more of the cultivation, production, processing, or sales of the *cannabis* products, or combinations thereof, meet a minimum standard of quality. In certain embodiments of the invention, this quality assurance ensures that the products from a particular producer, processor or seller meet the minimum standards set by the regulatory agencies or boards. In certain embodiments of the invention, this quality assurance ensures that the products from a particular producer, processor or seller meet the appropriate standards set by the regulatory agencies or boards. In certain embodiments of the invention, this quality assurance ensures that the products from a particular producer, processor or seller are consistent with the labeling on the product.

In certain embodiments of the invention, these samples are analyzed for their compliance with labeling and other regulatory guidelines 208. In certain embodiments of the invention, *cannabis* products are analyzed for compliance with guidelines for the nutrition facts panel, the ingredient statement and allergen declaration, the nutritional claims, the statement of identity, the net contents statement, the type size and placement requirements for the label, and combinations thereof.

In certain embodiments of the invention, users can access a variety of information, records, recommendations, and advisory reports, collectively described as user reports 209, resulting from the testing of the *cannabis* products. Users of certain embodiments of the invention can access a variety of information and reports 209, including, but not limited to, reports regarding the origin and processing records and the chemical and biological contents of the *cannabis* products submitted for testing. Certain embodiments of the invention include users like federal and state agencies or boards accessing the information to generate reports 209, including, but not limited to, reports regarding the various *cannabis* products available in the various industries, production and processing volumes of the various products, the producers of the various products, and their compliance to the laws and regulatory guidelines.

Certain embodiments of the invention involve the systems, computer-readable program product, and related computer-implemented methods to obtain information from the users and generate *cannabis* user reports, according to embodiments of the present invention as discussed above. These embodiments can be implemented using one or more computers, one or more servers, one or more databases, and one or more cloud computing configurations, and one or more communications networks. Certain embodiments of the invention include a system for collecting a plurality of information related to a *cannabis* product and maintaining a registry. The plurality of information includes but is not limited to information regarding *cannabis* production facilities, *cannabis* strains, *cannabis* products, associated test results and compliance certificates, *cannabis* processing and distribution systems, and ultimate consumers. The plurality of information can also include information from inventory tracking software, like Colorado's Marijuana Inventory Tracking Solution (MITS).

Certain embodiments of the invention include a system with one or more remote electronic interfaces configured to receive selection parameters entered by user and display a plurality of information related to one or more *cannabis* products. The system also has one or more databases that acquire and store the plurality of information related to one or more *cannabis* products and one or more processors in communication with the one or more databases. These processors are configured to acquire selection parameters entered by user through remote electronic interfaces, generate a data package from the plurality of information related to the *cannabis* product in the database responsive to the selection parameters entered by user and display the data package to the user responsive to the selection parameters entered by user through remote electronic interfaces.

Embodiments of the invention can include, for example, analyzing one or more *cannabis* products to determine the quality and quantity of desired components and undesired components in the one or more *cannabis* products using one or more of the following, for example: cannabinoid profiling, microbiological testing, analytical testing, food testing, acidified food testing, liquid testing, pathogen testing, quality control testing, quality assurance testing, or combinations thereof. Embodiments can further include, for example, determining concentration of one or more cannabinoids and determining the appropriate regulations for the *cannabis* products such as the relevant state regulations regarding the sale or consumption of *cannabis* products. Embodiments of the invention can further include comparing measurements of the quality and quantity of desired components and undesired components in the one or more *cannabis* products against state regulations for consumption of the one or more *cannabis* products and generating a report, for example, that includes if the *cannabis* product satisfied the appropriate regulations.

Figure 3:
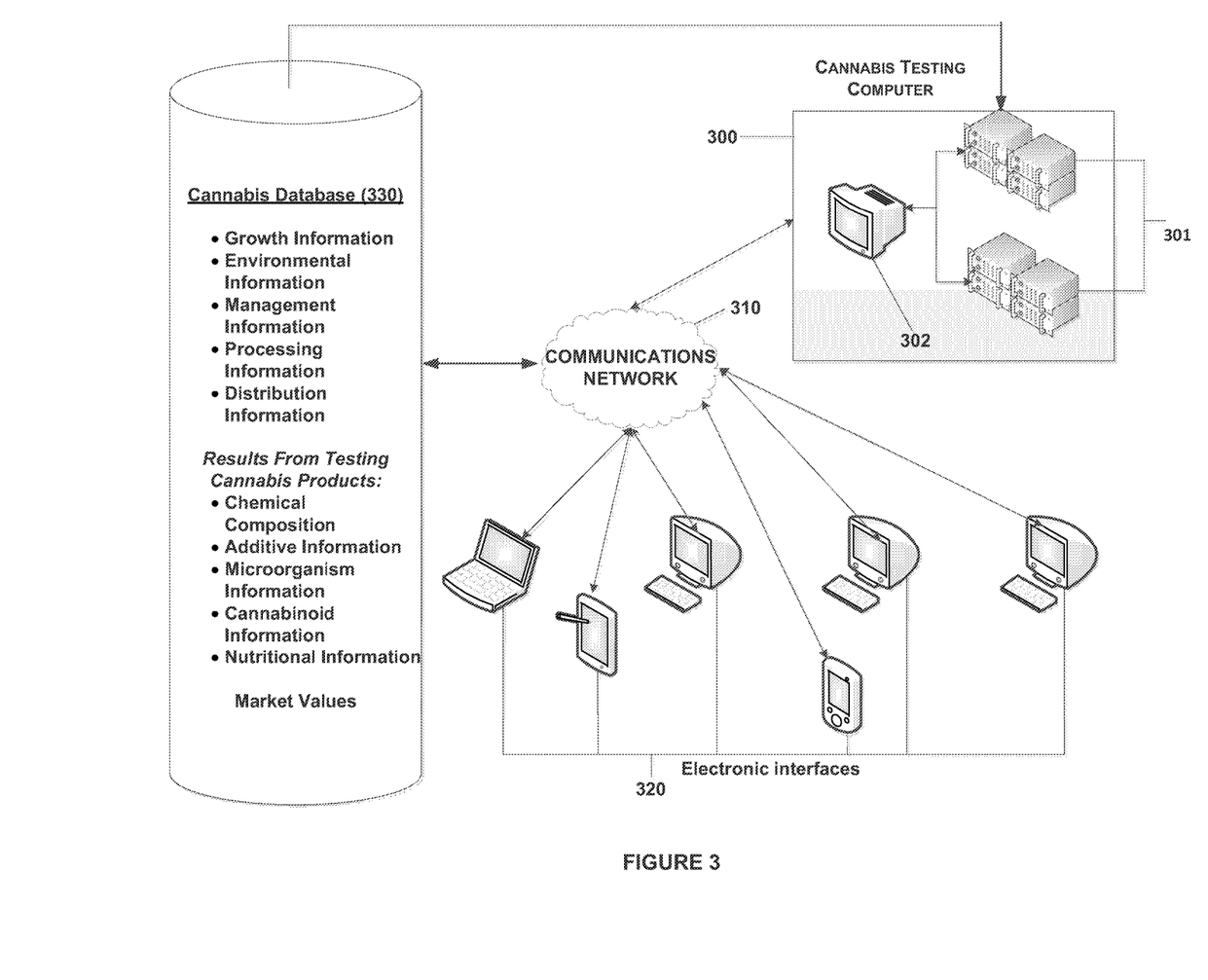
FIG. 3 is a schematic diagram of an exemplary system according to an embodiment of the invention.

FIG. 3 is an illustration of a system that is an exemplary embodiment of the invention. Such a system can include, for example, a communications network 310, a plurality of electronic interfaces 320, *cannabis* testing computer system 300, associated interfaces 302, associated servers 301, and a database 330. One or more entities can operate or control the *cannabis* testing computer system 300 that includes associated interfaces 302 and associated servers 301, with communication to a database 330, and a plurality of electronic interfaces 320. The communications network 310 can include a telephony network, a wireline network, a wireless network, a wide area network, a local area network, an infrared network, a radio-frequency network, an optical network, or any cloud computing configurations, or any other communications network now or hereinafter created as is known and understood by those skilled in the art. Each of the plurality of electronic interfaces 320 allows a human user, such as a producer, a processor, or a consumer, to interact with the *cannabis* testing computer system 300. Each of the electronic interfaces 320 allows such a human user, for example, to input information associated to one or more *cannabis* products as is described herein with respect to the *cannabis* testing system. Each of the electronic interfaces 320 allows such a human user, for example, to receive the *cannabis* user reports, and to access appropriate information from the *cannabis* testing system.

The reports from the *cannabis* testing system may be received by a user in a variety of formats, including, but not limited to, paper print-outs, graphical or text displays on a computer or mobile device, electronic messages like an e-mail or text, and other equivalent formats. The output from a *cannabis* testing system can include other techniques including updating a record in a database, updating a spreadsheet, and sending instructions and/or data to specialized software, such as an application on a mobile device, or combinations thereof. In other embodiments, the output from a *cannabis* testing system may include formats and reports stored on computer readable medium (such as a CD, DVD, USB flash drive, stand alone, or other removable storage device, computer hard drive, or computer network server, etc.). The output from a *cannabis* testing system, particularly those stored on computer readable medium, can be part of a database, which may optionally be accessible via the internet, such as a database of information regarding various *cannabis* products, the associated producers, processors or sellers stored on a computer network server. The database may be a secure database with security features that limit access to information regarding various *cannabis* products, such as to allow only authorized users to view them.

According to various exemplary embodiments of the present invention, the database 330 can be any database structure as is known and understood by those skilled in the art. The databases discussed herein, including database 330, can be, for example, any sort of organized collection of data in digital form. Databases, including database 330, can include the database structure as well as the computer programs that provide database services to other computer programs or computers, as defined by the client-server model, and any computer dedicated to running such computer programs (i.e., a database server). An exemplary database model, for example, is a Microsoft SQL Server 2014 CTP2 or SQL Server 2012, or SQL Server 2008 R2. Databases can include a database management system (DBMS) consisting of software that operates the database, provides storage, access, security, backup and other facilities. DBMS can support multiple query languages, including, for example, SQL, XQuery, OQL, LINQ, JDOQL, and JPAQL. Databases can implement any known database model or database models, including, for example, a relational model, a hierarchical model, a network model, or an object-oriented model. The DBMS can include Data Definition Language (DDL) for defining the structure of the database, Data Control Language (DCL) for defining security/access controls, and Data Manipulation Language (DML) for querying and updating data. The DBMS can further include interface drivers, which are code libraries that provide methods to prepare statements, execute statements, fetch results, etc. Examples of interface drivers include ODBC, JDBC, MySQL/PHP, FireBird/Python. DBMS can further include a SQL engine to interpret and execute the DDL, DCL, and DML statements, which includes a compiler, optimizer, and executor. DBMS can further include a transaction engine to ensure that multiple SQL statements either succeed or fail as a group, according to application dictates. DBMS can further include a relational engine to implement relational objects such as Table, Index, and Referential integrity constraints. DBMS can further include a storage engine to store and retrieve data from secondary storage, as well as managing transaction commit and rollback, backup and recovery, etc.

Data stored in fields of the databases can be updated as needed, for example, by a user with administrative access to the database to add new data to the libraries in the database as they become supported. It will be appreciated by those having skill in the art that data described herein as being stored in the databases can also be stored or maintained in non-transitory memory and accessed among subroutines, functions, modules, objects, program products, or processes, for example, according to objects and/or variables of such subroutines, functions, modules, objects, program products or processes. Any of the fields of the records, tables, libraries, and so on of the database can be multi-dimensional structures resembling an array or matrix and can include values or references to other fields, records, tables, or libraries. Any of the foregoing fields can contain either actual values or a link, a join, a reference, or a pointer to other local or remote sources for such values.

Database 330 can be, for example, a single database, multiple databases, or a virtual database, including data from multiple sources, for example, servers on the World Wide Web. The *cannabis* database 330 can contain several types of data, including, but not limited to, plant information associated with the *cannabis* products, growth information of the plants, environmental information, plant management information, raw material processing information, *cannabis* product distribution information, and results from testing *cannabis* products. These results from testing *cannabis* products can include, without limitations, chemical composition, additive information, microorganism information, cannabinoid profile, nutritional information, and market information. In certain embodiments of the invention, the market information can include historical sales data, sales projection data, and real-time market values for raw materials and processed *cannabis* products in a variety of industries. The plant information associated with the one or more *cannabis* products in the one or more *cannabis* databases includes one or more of: *cannabis* strain, source of seeds, genotype and phenotype of the plants associated with the one or more of the *cannabis* products, and combinations thereof. The environmental information associated with the one or more *cannabis* products in the one or more *cannabis* databases includes one or more of: germination conditions, location, temperature, water, exposure to light, and combinations thereof. The plant management information associated with the one or more *cannabis* products in the one or more *cannabis* databases includes one or more of: pesticide use, fertilizer use, growth pattern control, and combinations thereof. Database 330 can be the inventors' proprietary database or one populated with data from publicly available databases or a combination thereof.

According to various exemplary embodiments of the present invention, for example, and as illustrated by FIG. 3, the *cannabis* database 330 can be part of a data warehouse. Such a data warehouse may include other databases, for example, a user database, an administration database, content from or links to other public databases, a regulatory guidelines database, and/or a sales database. The user database can be configured, for example, to store any data related to user information, including user names, user addresses, state or federal authorization information, payment records, data related to user's products or consumption needs, and any other information related to a user, as is known and understood by those skilled in the art.

This application claims the benefit of and priority to U.S. Provisional Patent Application No. 61/936,200, filed on Feb. 5, 2014, and titled "Systems and Methods of Evaluating *Cannabis* Products for Public Safety, Quality Control and Quality Assurance Purposes"; and U.S. Provisional Patent Application No. 61/939,385, filed on Feb. 13, 2014, and titled "Systems and Methods of Evaluating *Cannabis* Products for Public Safety, Quality Control and Quality Assurance Purposes", the disclosures of which are each hereby incorporated by reference in their entireties.

Moreover, the foregoing has broadly outlined certain objectives, features, and technical advantages of the present invention and a detailed description of the invention so that embodiments of the invention may be better understood in light of features and advantages of the invention as described herein, which form the subject of certain claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features that are believed to be characteristic of the invention, both as to its organization and method of operation, together with further objects and advantages is better understood from the following description when considered in connection with the accompanying figures. It is to be expressly understood, however, that such description and figures are provided for the purpose of illustration and description only and are not intended as a definition of the limits of the present invention. It will be apparent to those skilled in the art that various modifications and changes can be made within the spirit and scope of the invention as described in the foregoing specification.

That claimed is:

1. A method for evaluating one or more *cannabis* products for consumption, the method comprising:
    analyzing one or more *cannabis* products to determine quality and quantity of desired components and undesired components in the one or more *cannabis* products using one or more of: cannabinoid profiling, microbiological testing, analytical testing, food testing, acidified food testing, liquid testing, pathogen testing, quality control testing, quality assurance testing, or combinations thereof;
    determining concentration of one or more cannabinoids in the one or more *cannabis* products;
    comparing measurements of the quality and quantity of desired components and undesired components and concentration of the one or more cannabinoids in the one or more *cannabis* products against state regulations for consumption of the one or more *cannabis* products to determine if the one or more *cannabis* products satisfies the state regulations for consumption; and
    labeling the one or more *cannabis* products with one or more visual indicators associated with the quality and quantity of desired components in the *cannabis* products in response to the one or more *cannabis* products having satisfied the state regulations for consumption.

2. The method of claim 1, wherein the method further includes:
    generating using one or more computers a report that includes the quality and quantity of desired components and undesired components in the one or more *cannabis* products.

3. The method of claim 1, further comprising the steps of serving to an electronic interface for display to a user a plurality of information associated with the one or more *cannabis* products.

4. The method of claim 3, wherein the plurality of information associated with the one or more *cannabis* products includes identity of the one or more *cannabis* products, source of the one or more *cannabis* products, the quality of desired components in the one or more *cannabis* products, and the quantity of desired components in the one or more *cannabis* products, and combinations thereof.

5. The method of claim 3, wherein the plurality of information associated with the one or more *cannabis* products includes the quantity of tetrahydrocannabinol in the one or more *cannabis* products.

6. The method of claim 3, wherein the plurality of information associated with the one or more *cannabis* products includes the quantity of cannabidiol in the one or more *cannabis* products.

7. An online *cannabis* testing system, the system comprising:
    one or more processors;
    one or more *cannabis* databases in communication with the one or more processors to store and associate a plurality of regulatory guidelines with a plurality of measurements of quality of desired components and undesired components in the one or more *cannabis* products and a plurality of measurements of quantity of desired components and undesired components in the one or more *cannabis* products;
    one or more electronic interfaces positioned to display a *cannabis* user report and defining one or more *cannabis* user interfaces; and
    a non-transitory computer-readable medium positioned in communication with the one or more processors and having one or more computer programs stored thereon including a set of instructions that when executed by one or more processors cause the one or more processors to perform operations of:
        generating the one or more *cannabis* user interfaces, the one or more *cannabis* user interfaces allowing an input of query parameters associated with the one or more *cannabis* products;
        retrieving, in response to the input of query parameters, a plurality of information associated with the one or more *cannabis* products from the one or more *cannabis* databases, the plurality of information including the plurality of measurements of quality of desired components and undesired components in the one or more *cannabis* products and the plurality of measurements of quantity of desired components and undesired components in the one or more *cannabis* products;
        determining whether the one or more *cannabis* products satisfy the plurality of regulatory guidelines responsive to receiving the query parameters and the plurality of information associated with the one or more *cannabis* products from the one or more *cannabis* databases;
        outputting to the one or more *cannabis* user interfaces the one or more *cannabis* user reports, the *cannabis* user reports including the plurality of information associated with the one or more *cannabis* products from the one or more *cannabis* databases and whether the one or more *cannabis* products satisfy the plurality of regulatory guidelines; and
        generating a label for the one or more *cannabis* products with one or more visual indicators associated with the plurality of measurements of quality of desired components and undesired components and the plurality of measurements of quantity of desired components and undesired components in the one or more *cannabis* products, in response to the one or more *cannabis* products having satisfied the plurality of regulatory guidelines.

8. The online *cannabis* testing system as defined in claim 7, wherein the *cannabis* user reports further include one or more of: identity of the one or more *cannabis* products, source of the one or more *cannabis* products, the plurality of measurements of the quality of desired components in the one or more *cannabis* products, the plurality of measurements of the quantity of desired components in the one or more *cannabis* products, and combinations thereof.

9. The online *cannabis* testing system as defined in claim 7, wherein the regulatory guidelines include state regulations for consumption of the one or more *cannabis* products.

10. The online *cannabis* testing system as defined in claim 7, wherein the regulatory guidelines include state regulations for distribution of the one or more *cannabis* products.

11. The online *cannabis* testing system as defined in claim 7, wherein the regulatory guidelines include state regulations for sale of the one or more *cannabis* products.

12. The online *cannabis* testing system as defined in claim 7, wherein the *cannabis* user report includes quantity of tetrahydrocannabinol in the one or more *cannabis* products.

13. The online *cannabis* testing system as defined in claim 7, wherein the *cannabis* user report includes quantity of cannabidiol in the one or more *cannabis* products.

14. A system for managing a plurality of information related to one or more *cannabis* products, comprising:
one or more processors;
one or more electronic interfaces configured to receive query parameters from a user and display one or more *cannabis* user reports associated with one or more *cannabis* products responsive to the query parameters from a user, thereby defining one or more *cannabis* user interfaces;
one or more *cannabis* databases in communication with the one or more processors to store a first plurality of information associated with the one or more *cannabis* products, the first plurality of information including identity of the one or more *cannabis* products, source of the one or more *cannabis* products, and a plurality of measurements of quality of desired components and undesired components in the one or more *cannabis* products, and a plurality of measurements of quantity of desired components and undesired components in the one or more *cannabis* products; and
non-transitory computer-readable medium positioned in communication with the one or more processors and having one or more computer programs stored thereon including a set of instructions that when executed by one or more processors cause the one or more processors to perform operations of:
receiving the first plurality of information associated with the one or more *cannabis* products from one or more data sources;
organizing the first plurality of information associated with the one or more *cannabis* products from one or more data sources in the one or more *cannabis* databases;
generating the one or more *cannabis* user interface, the one or more *cannabis* user interface allowing an input of one or more query parameters from the user;
retrieving a second plurality of information associated with the one or more *cannabis* products from the one or more *cannabis* databases, the second plurality of information being a subset of information from the first plurality of information associated with the one or more *cannabis* products generated in response to the query parameters from the user; and
determining whether the one or more *cannabis* products satisfy a plurality of regulatory guidelines responsive to the one or more query parameters from the user and the second plurality of information associated with the one or more *cannabis* products from the one or more *cannabis* databases;
generating one or more *cannabis* user reports based on the second plurality of information associated with the one or more *cannabis* products in the one or more *cannabis* databases, the one or more *cannabis* user reports containing one or more visual indicators of the quantity of one or more desired components in the one or more *cannabis* products and a certification of compliance for the one or more *cannabis* products if the one or more *cannabis* products satisfy a plurality of regulatory guidelines.

15. The system as defined in claim 14, wherein the query parameters from the user include one or more of the following: identity of the one or more *cannabis* products, source of the one or more *cannabis* products, one or more measurements of quality of desired components in the one or more *cannabis* products, one or more measurements of quantity of desired components in the one or more *cannabis* products, and combinations thereof.

16. The system as defined in claim 14, wherein the first plurality of information associated with the one or more *cannabis* products in the one or more *cannabis* databases includes one or more of the following: plant information, environmental information, plant management information, raw material processing information, *cannabis* product distribution information, and results from testing one or more *cannabis* products.

17. The system as defined in claim 16, wherein the plant information associated with the one or more *cannabis* products in the one or more *cannabis* databases includes one or more of: *cannabis* strain, source of seeds, genotype and phenotype of the plants associated with the one or more of the *cannabis* products, and combinations thereof.

18. The system as defined in claim 16, wherein the environmental information associated with the one or more *cannabis* products in the one or more *cannabis* databases includes one or more of: germination conditions, location, temperature, water, exposure to light, and combinations thereof.

19. The system as defined in claim 16, wherein the plant management information associated with the one or more *cannabis* products in the one or more *cannabis* databases includes one or more of: pesticide use, fertilizer use, growth pattern control, and combinations thereof.

20. The system as defined in claim 14, wherein the second plurality of information associated with the one or more *cannabis* products includes quantity of tetrahydrocannabinol in the one or more *cannabis* products.

21. The system as defined in claim 14, wherein the second plurality of information associated with the one or more *cannabis* products includes quantity of cannabidiol in the one or more *cannabis* products.

* * * * *